US008798733B2

(12) United States Patent
Wang et al.

(10) Patent No.: US 8,798,733 B2
(45) Date of Patent: Aug. 5, 2014

(54) DEVICE AND METHOD FOR IDENTIFYING CARDIAC EVENTS

(75) Inventors: Hanbiao Wang, Woodland Hills, CA (US); Bonian Dai, Temple City, CA (US); Iman Ahmadi, Valencia, CA (US); Erik Brockman, Saratoga, CA (US)

(73) Assignee: Pacesetter, Inc., Sylmar, CA (US)

( * ) Notice: Subject to any disclaimer, the term of this patent is extended or adjusted under 35 U.S.C. 154(b) by 164 days.

(21) Appl. No.: 12/755,348

(22) Filed: Apr. 6, 2010

(65) Prior Publication Data
US 2011/0245698 A1    Oct. 6, 2011

(51) Int. Cl.
  *A61B 5/0452*    (2006.01)
  *A61B 5/0468*    (2006.01)
  *A61B 5/0472*    (2006.01)

(52) U.S. Cl.
  CPC .............. *A61B 5/0452* (2013.01); *A61B 5/0468* (2013.01); *A61B 5/0472* (2013.01)
  USPC .......................................... 600/516; 600/509

(58) Field of Classification Search
  CPC ... A61B 5/0452; A61B 5/0468; A61B 5/0472
  USPC .......................................... 600/509
  See application file for complete search history.

(56) References Cited

U.S. PATENT DOCUMENTS

| 5,701,907 | A  | * | 12/1997 | Klammer ...................... 600/509 |
| 6,625,484 | B2 | * | 9/2003  | Kohler et al. ................. 600/521 |
| 6,658,286 | B2 | * | 12/2003 | Seim ............................ 600/516 |
| 2007/0197929 | A1 | * | 8/2007 | Porath et al. .................. 600/523 |

OTHER PUBLICATIONS

Brockman, Erik, "Time-Frequency Analysis of Intracardiac Electrogram," Jun. 2009: A Thesis presented to the Faculty of California Polytechnic State University.

* cited by examiner

*Primary Examiner* — Christopher D Koharski
*Assistant Examiner* — Philip Edwards

(57) ABSTRACT

An implantable medical device includes leads having electrodes that are positioned within a heart. The electrodes sense signals derived from the heart that include waveform segments. The device includes a timing module that determines when the waveform segments cross a threshold and measures time intervals between at least two threshold crossings by the waveform segments. The device also includes event identification module that compares the time intervals to a predetermined pattern associated with a cardiac event. The event identification module identifies the cardiac event based on the time intervals and the predetermined pattern.

17 Claims, 6 Drawing Sheets

US 8,798,733 B2

DEVICE AND METHOD FOR IDENTIFYING CARDIAC EVENTS

FIELD OF THE INVENTION

Embodiments described herein generally pertain to implantable medical devices and more particularly to methods and systems that identify cardiac events such as waveform segments based on signals derived from a heart.

BACKGROUND OF THE INVENTION

An implantable medical device (IMD) is implanted in a patient to monitor, among other things, electrical activity of a heart and to deliver appropriate electrical therapy, as required. IMDs include pacemakers, cardioverters, defibrillators, implantable cardioverter defibrillators (ICD), and the like. The electrical therapy produced by an IMD may include pacing pulses, cardioverting pulses, and/or defibrillator pulses to reverse arrhythmias (e.g., tachycardias and bradycardias) or to stimulate the contraction of cardiac tissue (e.g., cardiac pacing) to return the heart to its normal sinus rhythm. These pulses are referred to as stimulus or stimulation pulses.

In order to determine when stimulus pulses are to be applied to the heart, the IMDs identify cardiac events of the heart and, based on the cardiac events, supply or withhold the stimulus pulses to the heart. By way of example, the cardiac events may include cardiac signal waveform segments, segments of cardiac signals between waveform segments, heart rates, and the like.

The accurate identification of cardiac events is desirable to ensure that stimulus pulses are applied to the heart when needed and are withheld when unnecessary. Some known IMDs use time-domain processing techniques to identify cardiac events. For example, the IMDs may compare the cardiac signals to a threshold and classify the cardiac signals as indicative of a cardiac event every time the cardiac signals extend above the threshold. But, identifying cardiac events based on comparisons between cardiac signals and a threshold can be prone to errors. For example, in some patients a QRS complex may be misidentified as a T-wave, and vice-versa.

The battery energy reserves of some known IMDs limit the amount of computational resources that are implemented in analysis methods that may be used by the IMDs to identify cardiac events based on cardiac signals. For example, the battery energy reserves of some known IMDs are too small to permit the IMDs to engage in costly frequency domain processing techniques such as Fourier transforms and wavelet transforms. As a result, some known IMDs are limited to the simple time-domain processing techniques such as comparing cardiac signals to a single threshold.

A need exists for an IMD that more accurately identifies cardiac events while avoiding costly processing techniques that consume the battery energy reserves of the IMDs.

BRIEF SUMMARY OF THE INVENTION

In one embodiment, an implantable medical device is provided. The implantable medical device includes leads having electrodes that are positioned within a heart. The electrodes sense signals derived from the heart that include waveform segments. The device includes a timing module that determines when the waveform segments cross a threshold and measures time intervals between at least two threshold crossings by the waveform segments. The device also includes event identification module that compares the time intervals to a predetermined pattern associated with a cardiac event. The event identification module identifies the cardiac event based on the time intervals and the predetermined pattern.

In another embodiment, a method for identifying cardiac events is provided. The method includes sensing signals derived from a heart that include waveform segments and determining when the waveform segments cross a threshold. The method also includes measuring time intervals between at least two threshold crossings by waveform segments and comparing the time intervals to a predetermined pattern associated with the cardiac event. The method further includes identifying the cardiac event based on the time intervals and the predetermined pattern.

In another embodiment, a computer-readable storage medium for use in a medical device having a memory and a programmable controller is provided. The computer readable storage medium includes instructions to direct the memory to store a threshold, a pattern, and signals having waveform segments that are derived from a heart. The instructions also direct the controller to determine when the waveform segments cross a threshold and measure time intervals between at least two crossings of the threshold by the waveform segments. The instructions further direct the controller to compare the time intervals to the pattern that is associated with a cardiac event and to identify the cardiac event based on the time intervals and the pattern.

BRIEF DESCRIPTION OF THE DRAWINGS

The drawings illustrate generally, by way of example, but not by way of limitation, various embodiments discussed in the present document.

DETAILED DESCRIPTION OF THE INVENTION

In the following detailed description, reference is made to the accompanying drawings which form a part hereof, and in which are shown by way of illustration specific embodiments in which the present invention may be practiced. These embodiments, which are also referred to herein as "examples," are described in sufficient detail to enable those skilled in the art to practice the invention. It is to be understood that the embodiments may be combined or that other embodiments may be utilized, and that structural, logical, and electrical variations may be made without departing from the scope of the present invention. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

In accordance with certain embodiments, methods and systems are provided for identifying cardiac events by determining dominant frequencies of signals derived or obtained from a heart. By way of example only, the signals may include electric signals, such as waveform segments of an internal EGM. The waveforms may be QRS complexes, T-waves, QT intervals, and the like. The signals may include or be based on other signals derived from activities of the heart, such as heart sounds, cardiogenic impedance measurements of the heart, blood pressure of the heart, oxygenation levels, and the like. The dominant frequencies of the signals may be determined by measuring the time periods over which the signals extend above or below predetermined thresholds. By way of example only, a dominant frequency of a T-wave in signals may be based on the time period that the T-wave extends above a threshold before subsequently falling below the threshold. Identifying events using the dominant frequencies of the signals may be more accurate than identifying signals based on, for example, the amplitudes of signal waveform segments. In one embodiment, identifying cardiac events using the dominant frequencies may result in less battery power of the IMD being consumed to identify the cardiac events.

Figure 1:
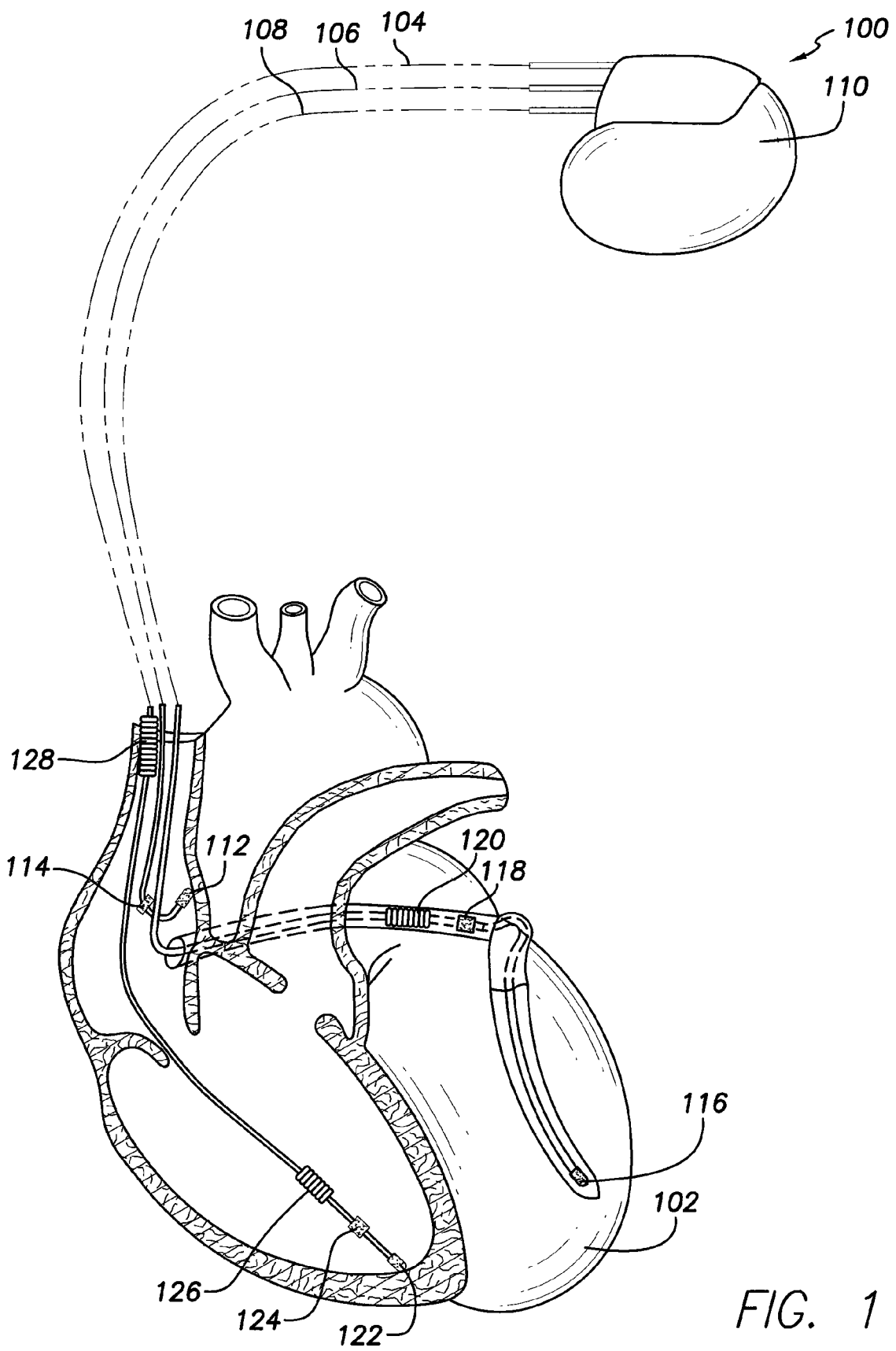
FIG. 1 illustrates an implantable medical device (IMD) coupled to a heart in accordance with one embodiment.

FIG. 1 illustrates an implantable medical device (IMD) 100 coupled to a heart 102 in accordance with one embodiment. The IMD 100 may be a cardiac pacemaker, an ICD, a defibrillator, an ICD coupled with a pacemaker, a cardiac resynchronization therapy (CRT) pacemaker, a cardiac resynchronization therapy defibrillator (CRT-D), and the like. The IMD 100 includes a housing 110 that is joined to several leads 104, 106, 108. The leads 104, 106, 108 are located at various locations of the heart 102, such as an atrium, a ventricle, or both, to measure cardiac signals of the heart 102. The leads 104, 106, 108 include the right ventricular (RV) lead 104, the right atrial (RA) lead 106, and the left ventricular (LV) lead 108. Several electrodes 112, 114, 116, 118, 120, 122, 124, 126, 128 are coupled with the leads 104, 106, 108 for sensing signals of the heart 102 and/or for delivering stimulus or stimulation pulses to the heart 102. The housing 110 may be one of the electrodes and is often referred to as the "can", "case", or "case electrode."

The RV lead 104 is coupled with an RV tip electrode 122, an RV ring electrode 124, and an RV coil electrode 126. The RV lead 104 may include a superior vena cava (SVC) coil electrode 128. The right atrial lead 106 includes an atrial tip electrode 112 and an atrial ring electrode 114. The LV lead 108 includes a left ventricular (LV) tip electrode 116, a left atrial (LA) ring electrode 118 and an LA coil electrode 120. Alternatively, the LV lead 108 may be a quadropole lead that includes several electrodes disposed within the left ventricle. Leads and electrodes other than those shown in FIG. 1 may be included in the IMD 100 and positioned in or proximate to the heart 102.

The IMD 100 monitors signals derived from or based on activity of the heart 102 to determine if and when to deliver stimulus pulses to one or more chambers of the heart 102. As described above, the signals that are monitored by the IMD 100 may include, by way of example only, electric cardiac signals such as internal EGMs, heart sounds, cardiogenic impedance measurements, blood pressures, oxygenation levels, and the like. The IMD 100 may deliver pacing stimulus pulses to pace the heart 102 and maintain a desired heart rate and/or shocking stimulus pulses to treat an abnormal heart rate such as tachycardia or bradycardia. The IMD 100 may determine when the heart rate differs from the desired heart rate or when the heart rate is abnormal based on the frequency or rate at which certain signal waveform segments occur, such as internal EGM waveform segments. As described below, in order to accurately identify heart rates, the IMD 100 identifies dominant frequencies of the signals related to and/or sensed from activity of the heart.

Figure 2:
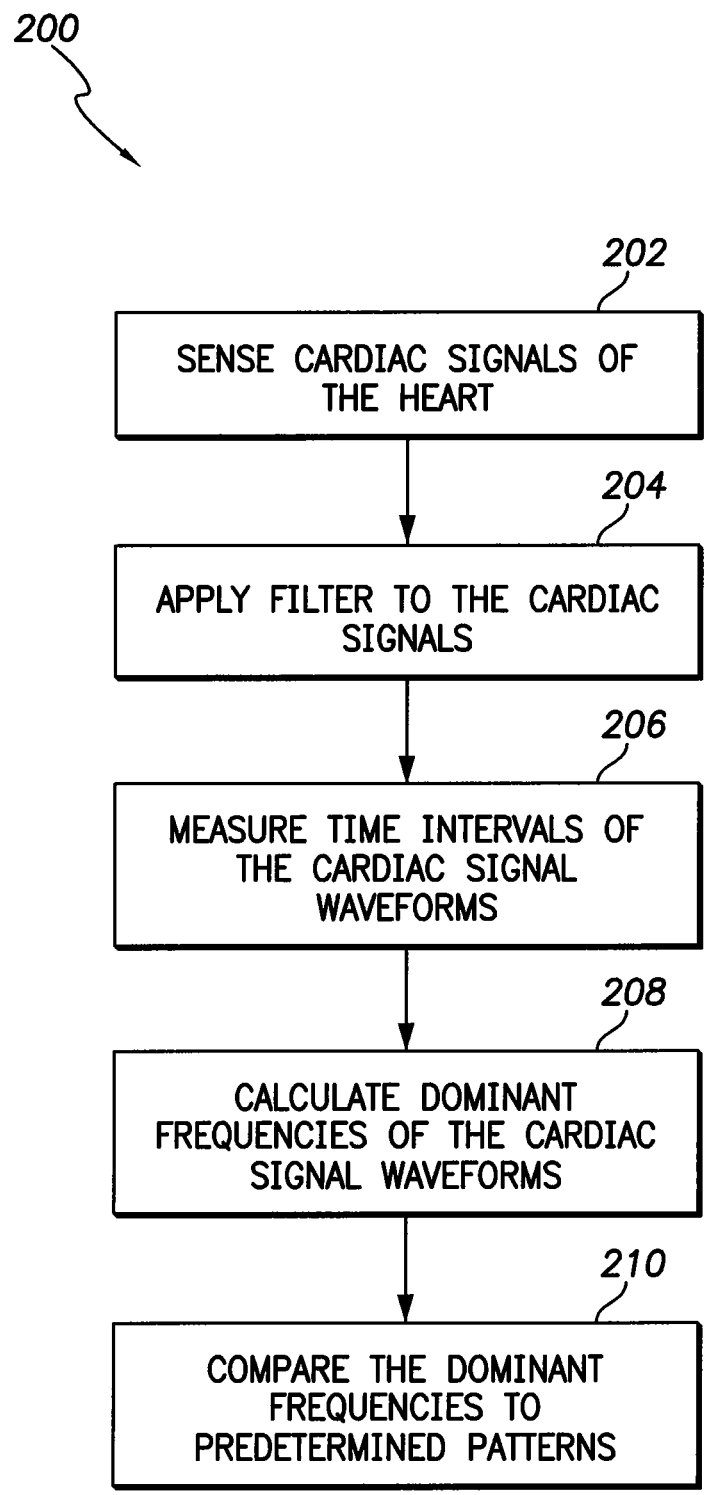
FIG. 2 is a flowchart of a method for identifying cardiac events in accordance with one embodiment.

FIG. 2 is a flowchart of a method 200 for identifying cardiac events in accordance with one embodiment. The method 200 identifies cardiac events, such as heart rates, cardiac signal waveform segments, and the like, by identifying dominant frequencies of signals obtained or derived from the heart 102 (shown in FIG. 1) and/or activity of the heart 102. At 202, signals of the heart 102 (shown in FIG. 1) are sensed. The signals may be electric signals, such as internal EGM signals, heart sounds, cardiogenic impedance measurements, blood pressure measurements, oxygenation levels, and the like. The signals may be sensed using the leads 104-108 (shown in FIG. 1) and electrodes 112-128 (shown in FIG. 1). Alternatively, the signals may be measured or sensed using other sensors. For example, heart sounds may be obtained by an acoustic sensor of the IMD 100. The flowchart of FIG. 2 will be described in connection with FIG. 3.

Figure 3:
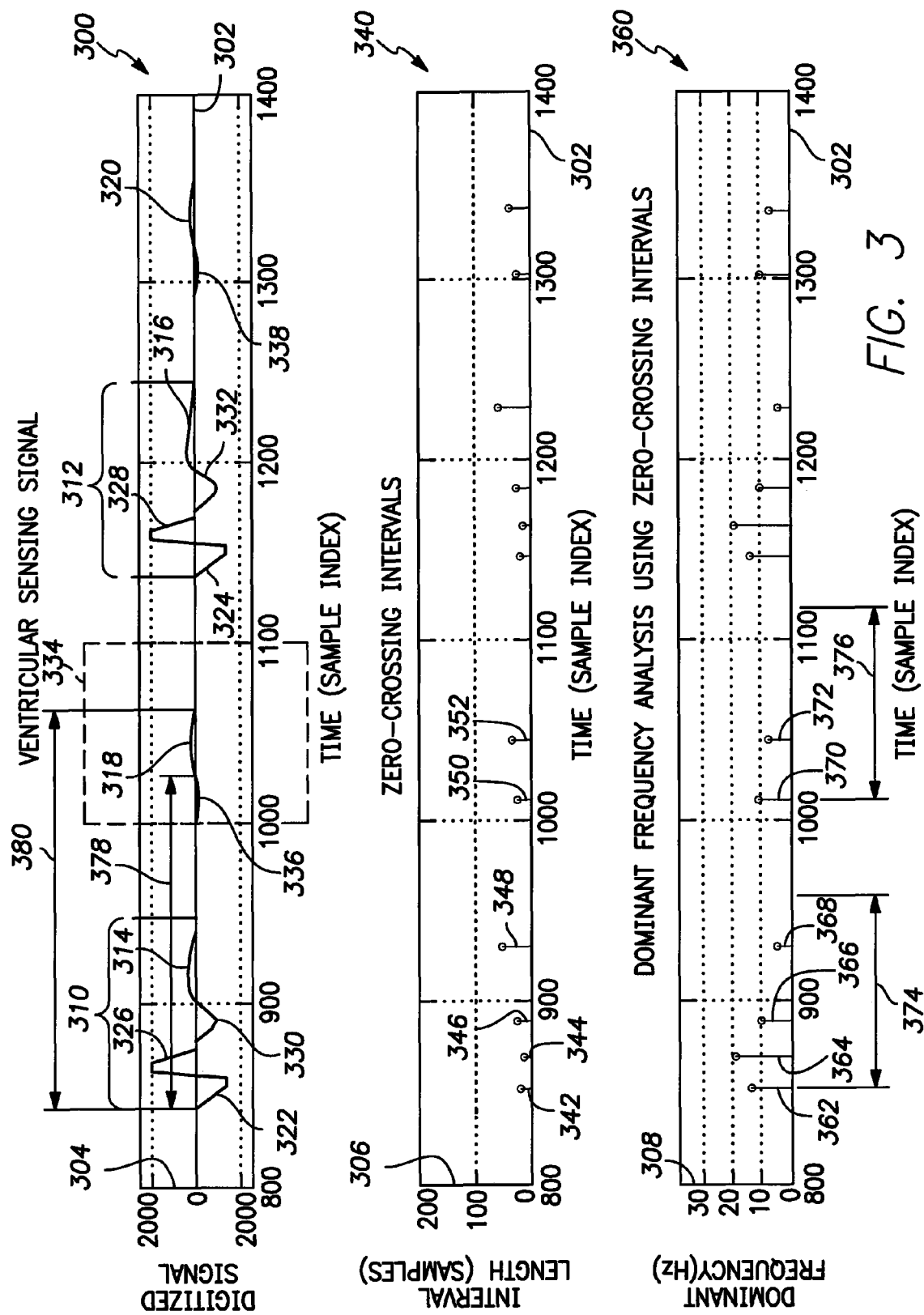
FIG. 3 illustrates cardiac signals obtained from the heart shown alongside a waveform interval set and dominant frequency set in accordance with one embodiment.

FIG. 3 illustrates signals 300 obtained from the heart 102 shown alongside a waveform interval set 340 and dominant frequency set 360 that are derived from the signals 300 in accordance with one embodiment. In the illustrated embodiment, the signals 300 are internal EGM signals that include waveform segments 314, 316, 318, 320, 322, 324, 326, 328, 330, 332, 336, and 338 that combine to define the QRS complex and T-wave. The waveform interval set 340 includes time intervals 342, 344, 346, 348, 350, and 352. The dominant frequency set 360 includes dominant frequencies 362, 364, 366, 368, 370, and 372.

Each of the signals 300, the waveform interval set 340, and dominant frequency set 360 is shown alongside a horizontal axis 302 representative of time. The signals 300 are shown next to a vertical axis 304 that represents the amplitude of the signals 300. The amplitude of the cardiac signals 300 may be expressed in terms of millivolts. The waveform interval set 340 is shown alongside a vertical axis 306 that represents time periods of waveform segments in the signals 300. The dominant frequency set 360 is shown next to a vertical axis 308 that represents frequencies of waveform segments in the signals 300.

The signals 300 represent ventricular sensing signals that are obtained over at least two cardiac cycles of the heart 102 (shown in FIG. 1) and include several waveform segments. FIG. 3 illustrates first and second QRS complexes 310, 312 and first and second T-waves 318, 320. The QRS complexes 310, 312 include Q-waves 322, 324, R-waves 326, 328, and S-waves 330, 332. In the illustrated examples, the S-waves 330, 332 are followed by positive waveform segments 314, 316 and the T-waves 318, 320 have preceding negative waveform segments 336, 338. While the waveform interval set 340 and the dominant frequency set 360 shown in FIG. 3 extend over two cardiac cycles, alternatively the waveform interval set 340 and dominant frequency set 360 may extend over a shorter or longer period of time.

Returning to the discussion of the method 200 shown in FIG. 2 but with continued reference to FIG. 3, at 204, a filter is applied to the signals 300. The filter may remove portions of the signals 300. For example, the filter may be a band pass filter that removes portions of the signals 300 that fall within the band pass filter.

Figure 4:
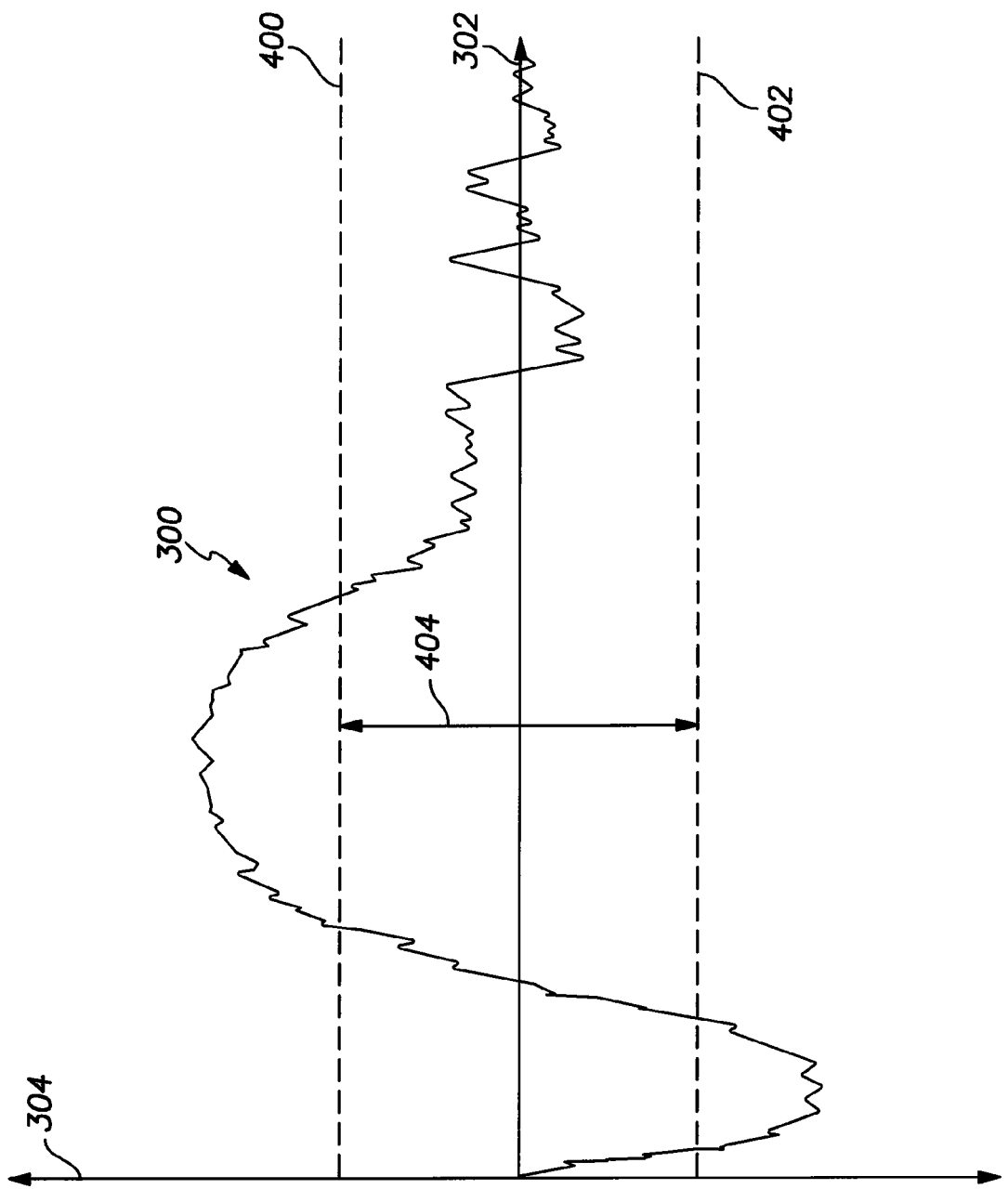
FIG. 4 is an enlarged view of a section of the cardiac signals shown in FIG. 3 in accordance with one embodiment.

FIG. 4 is an enlarged view of a section of the signals 300 shown in FIG. 3 in accordance with one embodiment. The section of the signals 300 shown in FIG. 3 corresponds to the portion identified as section 334 in FIG. 3. FIG. 4 illustrates the use of a filter to exclude portions of the signals 300 from the identification of signal waveform segments 310, 312, 314, 316, 318, 320, 322, 324, 326, 328, 330, 332, 336, 338 (shown in FIG. 3), the time intervals 342, 344, 346, 348, 350, 352 of the waveform interval set 340 (shown in FIG. 3), and/or the dominant frequencies 362, 364, 366, 368, 370, 372 of the dominant frequency set 360 (shown in FIG. 3). As with FIG. 3, the signals 300 are shown alongside the horizontal and vertical axes 302, 304 in FIG. 4.

The filter extends between an upper threshold 400 and a lower threshold 402. The upper and lower thresholds 400, 402 may be relatively small in value such that the upper and lower thresholds 400, 402 are located near the horizontal axis 302. By way of example only, the upper threshold 400 may have a value of +0.1 millivolts and the lower threshold 402 may have a value of −0.1 millivolts. Alternatively, the upper and lower thresholds 400, 402 may have different values. In one embodiment, the upper and/or lower thresholds 400, 402 may be adjusted based on a shift in the baseline of the signals 300.

The area within the filter between the upper and lower thresholds 400, 402 is referred to as a zero zone 404. Signals 300 that fall within the zero zone 404 are treated as having a value of zero. For example, the signals 300 within the zero zone 404 may be ignored during the measuring of time intervals 342, 344, 346, 348, 350, 352 (shown in FIG. 3) and/or the identification of dominant frequencies 362, 364, 366, 368, 370, 372 (shown in FIG. 3) of the signals 300. The signals 300 within the zero zone 404 are ignored so that minor fluctuations in the signals 300 or noise are not treated or considered as signal waveform segments 310, 312, 314, 316, 318, 320, 322, 324, 326, 328, 330, 332, 336, 338 (shown in FIG. 3).

Returning to the discussion of the method 200 shown in FIG. 2 with continued reference to FIG. 3, at 206, time intervals of the signal waveform segments 310, 312, 314, 316, 318, 320, 322, 324, 326, 328, 330, 332 are measured. The time interval of a waveform segment 310, 312, 314, 316, 318, 320, 322, 324, 326, 328, 330, 332 represents the time period over which the waveform segment 310, 312, 314, 316, 318, 320, 322, 324, 326, 328, 330, 332 extends above or below the zero zone 404 (shown in FIG. 4). The time intervals shown in FIG. 3 are represented in terms of samples of the signals 300 associated with one or more waveform segments 310, 312, 314, 316, 318, 320, 322, 324, 326, 328, 330, 332, 336, 338. For example, the vertical axis 306 represents an interval length of one or more waveform segments 310, 312, 314, 316, 318, 320, 322, 324, 326, 328, 330, 332, 336, 338. The interval length may be measured as the number of samples of the signals 300 obtained by the IMD 100 (shown in FIG. 1) for each waveform segment 310, 312, 314, 316, 318, 320, 322, 324, 326, 328, 330, 332, 336, 338. The IMD 100 may sample the signals 300 at a rate of once per 2.5 milliseconds, or at a frequency of 400 Hz. A waveform segment 310, 312, 314, 316, 318, 320, 322, 324, 326, 328, 330, 332, 336, 338 that is associated with a larger sample size means that the waveform segment 310, 312, 314, 316, 318, 320, 322, 324, 326, 328, 330, 332, 336, 338 extended above or below the zero zone 404 for a longer period of time than a waveform segment 310, 312, 314, 316, 318, 320, 322, 324, 326, 328, 330, 332, 336, 338 that has a smaller sample size.

In the illustrated embodiment, a time interval 342 corresponds to the Q-wave 322, a time interval 344 corresponds to the R-wave 326, a time interval 346 corresponds to the S-wave 330, and a time interval 348 corresponds to the positive waveform segment 314 of the first QRS complex 310. The time intervals 342, 344, 346, 348 represent the time periods between consecutive threshold crossings of the zero zone 404 (shown in FIG. 4) by a waveform segment. The time intervals 342, 346 may be referred to as negative zone intervals as the time intervals 342, 346 represent the time periods during which the corresponding Q-wave 322 and S-wave 330 extend below the zero zone 404 shown in FIG. 4. The time intervals 344, 348 may be referred to as positive zone intervals as the time intervals 344, 348 represent the time periods during which the corresponding R-wave 326 and positive waveform segment 314 extend above the zero zone 404.

In order to measure a time interval of a waveform segment 310, 312, 314, 316, 318, 320, 322, 324, 326, 328, 330, 332, 336, 338, the time or sample size that extends between at least two thresholds or zero crossings is determined. For example, the time or sample size that the waveform segment 310, 312, 314, 316, 318, 320, 322, 324, 326, 328, 330, 332, 336, 338 is in the positive zone above the zero zone 404 (shown in FIG. 4) or in the negative zone below the zero zone 404 may be calculated. In one embodiment, the time intervals 342, 344, 346, 348 are determined by measuring the time between a waveform segment exiting out of and rising above the zero zone 404 and then dropping into the zero zone 404, or by measuring the time between a waveform segment exiting out of and dropping below the zero zone 404 and then rising into the zero zone 404. When the waveform segment crosses the upper or lower thresholds 400, 402 (shown in FIG. 4) of the zero zone 404, this is referred to as a threshold or zero crossing.

In the illustrated embodiment, the time interval 342 represents the time between at least two threshold or zero crossings of the Q-wave 322. For example, the time interval 342 may be the time between the Q-wave falling below and crossing the lower threshold 402 (shown in FIG. 4) of the zero zone 404 (shown in FIG. 4) and the Q-wave 322 rising above and crossing the lower threshold 402. Similarly, the time interval 344 represents the time between threshold or zero crossings of the R-wave 326, or the time between the R-wave 326 rising above the upper threshold 400 and then falling below the upper threshold 400. The time interval 346 represents the time between threshold or zero crossings for the S-wave 330. The time interval 348 represents the time between threshold or zero crossings for the positive waveform segment 314.

As shown in the waveform interval set 340, the positive waveform segment 314 has the largest time interval 348 of the QRS complex 310. The positive waveform segment 314 having the largest time interval 348 indicates that the positive waveform segment 314 rose above or fell below the zero zone 404 (shown in FIG. 4) for the longest period of time of the waveform segments 314, 322, 326, 330 in the QRS complex 310. As shown in the signals 300, the positive waveform segment 314 does exceed the zero zone 404 longer than the Q-wave 322 or S-wave 330 fell below the zero zone 404 and longer than the R-wave 326 exceeded the zero zone 404. Similar time intervals 350, 352 may be determined for the negative waveform segment 336 and the T-wave 318, among other waveform segments.

Alternatively, the time intervals 342, 344, 346, 348, 350, 352 may be determined by measuring the time periods between consecutive crossings of the waveform segments 322, 326, 330, 314, 336, 318 across a single threshold. For example, instead of measuring the time intervals 342, 344, 346, 348, 350, 352 as time periods between consecutive crossings into or out of the zero zone 404 (shown in FIG. 4), the time intervals 342, 344, 346, 348, 350, 352 may be measured as the time periods between consecutive crossings of a single threshold.

At 208, the dominant frequencies 362, 364, 366, 368, 370, 372 of the dominant frequency set 360 are determined based on the time intervals 342, 344, 346, 348, 350, 352 of the waveform interval set 340. The dominant frequencies 360 include a set of dominant frequencies 362, 364, 366, 368, 370, 372 that correspond to the signals 300. The different dominant frequencies 362, 364, 366, 368, 370, 372 correspond to the different time intervals 342, 344, 346, 348, 350, 352 and waveform segments 322, 326, 330, 314, 336, 318. The dominant frequency of a waveform segment represents the frequency of the waveform segment that has the largest power density of all frequencies that may be associated with the waveform segment.

In one embodiment, the dominant frequencies 362, 364, 366, 368, 370, 372 of the waveform segments 322, 326, 330, 314, 336, 318 may be calculated based on the time intervals 342, 344, 346, 348, 350, 352 of the waveform segments 322, 326, 330, 314, 336, 318. By way of example only, the dominant frequency of a waveform segment may be calculated as a frequency of the time interval for the waveform segment as follows:

$$f = \frac{1}{A \times t} \quad \text{(Eqn. 1)}$$

where f represents the dominant frequency of a waveform segment, A represents a coefficient, and t represents the time interval of the waveform segment. In one embodiment, the coefficient "A" may have a predetermined value of 2, although a different value may be used. Alternatively, the dominant frequency may be calculated or derived in a different manner, such as by using a fast Fourier transform (FFT) or a Fourier transform (FT).

In the example signals 300 shown in FIG. 3, the negative waveform segment 336 has an interval length 350 of approximately 20 samples. At a sampling rate of 400 Hz, the negative waveform segment 336, corresponding to the interval length 350, has a time interval of approximately 20 samples. Accordingly, the time interval of the interval length 350 is approximately 0.05 seconds. Using Equation 1 above with the coefficient "A" having a value of 2, the dominant frequency 370 of the negative waveform segment 336 is approximately 10 Hz. In another example, the R-wave 326 has an interval length 344 of approximately 10 samples. At the sampling rate of 400 Hz, the interval length 344 has a time interval of approximately 10 samples. According, the time interval of the interval length 344 is approximately 0.025 seconds. Using Equation 1 above, the dominant frequency 364 of the R-wave 326 is approximately 20 Hz. The dominant frequencies 362, 366, 368, 372 of the other waveform segments 322, 330, 314, 318 may be calculated in a similar manner.

At 210, two or more of the dominant frequencies 362, 364, 366, 368, 370, 372 in the dominant frequency set 360 are compared to one or more patterns of dominant frequencies. A pattern of dominant frequencies may be a number of dominant frequencies occurring within a predetermined time window 374, 376. First and second time windows 374, 376 are shown in FIG. 3 as each extending over approximately 100 milliseconds. Alternatively, the time windows 374, 376 may extend over a shorter or longer length of time.

Different patterns may represent different cardiac events. By way of example only, a pattern of four dominant frequencies occurring during a time window 374 or 376 may be associated with a QRS complex while a pattern of two dominant frequencies occurring within the time window 374 or 376 may be associated with a T-wave. Other patterns of dominant frequencies may be used to identify cardiac events such as waveform segments. In another example, a pattern may be represented by the magnitude or amplitude of one or more dominant frequencies. The magnitude of one or more dominant frequencies in the pattern may be compared to a predetermined threshold. If the magnitude of the dominant frequency or frequencies exceeds the threshold(s) of the pattern, then the magnitude(s) of the dominant frequency or frequencies may be associated with a particular cardiac event.

In the embodiment shown in FIG. 3, upon the detection of the dominant frequency 362, the IMD 100 (shown in FIG. 1) begins counting the number of dominant frequencies 362, 364, 366, 368, 370, 372 that occur within the first time window 374. Four dominant frequencies 362, 364, 366, 368 occur before expiration of the first time window 374. Therefore, the IMD 100 determines that the dominant frequencies 362, 364, 366, 368 match the pattern of four dominant frequencies but not the pattern of two dominant frequencies. In the illustrated embodiment, the pattern of four dominant frequencies is associated with a QRS complex. As a result, the IMD 100 determines that the dominant frequencies 362, 364, 366, 368 are representative of the QRS complex 310.

In another example, after expiration of the first time window 374, the IMD 100 (shown in FIG. 1) begins the second time window 376 when the dominant frequency 370 is detected. The IMD 100 identifies two dominant frequencies 370, 372 as occurring within the second time window 376. The pattern of two dominant frequencies occurring within a time window 374, 376 indicates that the dominant frequencies 370, 372 are representative of the T-wave 318.

The dominant frequencies 362, 364, 366, 368, 370, 372 may be used to identify cardiac events other than waveform segments. For example, the dominant frequencies 362, 364, 366, 368, 370, 372 may be used to identify cardiac events such as an ST segment 378 or a QT interval 380. As shown in the signals 300, the ST segment 378 is the length of time between the end of the QRS complex 310 and the beginning of the T-wave 318. The QT interval 380 extends from the beginning of the QRS complex 310 to the end of the T-wave 318. The IMD 100 (shown in FIG. 1) may identify the ST segment 378 by comparing dominant frequencies 362, 364, 366, 368, 370, 372 to predetermined patterns in order to discern the occurrence of the QRS complex 310 and the T-wave 318, as described above.

Once the QRS complex 310 and the T-wave 318 are identified, the IMD 100 (shown in FIG. 1) determines when the beginning of the QRS complex 310 and the beginning of the T-wave 318 occur. The beginning of the QRS complex 310 may be identified by determining when the first time interval 342 associated with the QRS complex 310 begins. For example, the IMD 100 may determine when the signals 300 associated with the time interval 342 first extend below the zero zone 404 (shown in FIG. 4). The beginning of the T-wave 318 may be identified by determining when the time interval 372 associated with the T-wave 318 begins. For example, the IMD 100 may determine when the signals 300 associated with the time interval 352 first extend above the zero zone 404 (shown in FIG. 4). The time period extending from the beginning of the time interval 342 and the beginning of the time interval 352 may be the ST segment 378.

The IMD 100 (shown in FIG. 1) may identify the QT interval 380 by comparing dominant frequencies 362, 364, 366, 368, 370, 372 to predetermined patterns in order to discern the occurrence of the QRS complex 310 and the T-wave 318, as described above. Once the QRS complex 310 and the T-wave 318 are identified, the IMD 100 (shown in FIG. 1) determines when the beginning of the QRS complex 310 and the end of the T-wave 318 occur. The beginning of the QRS complex 310 may be identified as described above. The end of the T-wave 318 may be identified by determining when the time interval 372 associated with the T-wave 318 ends. For example, the IMD 100 may determine when the signals 300 associated with the time interval 352 first fall below the zero zone 404 (shown in FIG. 4) after rising above the zero zone 404 at the beginning of the time interval 352. The time period extending from the beginning of the time interval 342 and the end of the time interval 352 may be the QT interval 380.

In another embodiment, the IMD 100 (shown in FIG. 1) may use the time intervals 342, 344, 346, 348, 350, 352 to identify cardiac events without calculating the dominant frequencies 362, 364, 366, 368, 370, 372. For example, instead of calculating the dominant frequencies 362, 364, 366, 368, 370, 372 and comparing the dominant frequencies 362, 364, 366, 368, 370, 372 to predetermined patterns in order to identify cardiac events, the IMD 100 may compare the time intervals 342, 344, 346, 348, 350, 352 to predetermined patterns to identify cardiac events. By way of example only, the IMD 100 may compare the time intervals 342, 344, 346, 348 that occur over the first time window 374 in order to identify the QRS complex 310 and the time intervals 350, 352 that occur over the second time window 376 in order to identify the T-wave 318.

While the discussion herein focuses on the identification of cardiac events by measuring time intervals of signal waveform segments, calculating dominant frequencies based on the time intervals, and comparing the dominant frequencies to a predetermined pattern, alternatively one or more embodiments discussed herein may be used on other signals. For example, the identification of events, dominant frequencies, and/or time intervals may be used on other types of non-cardiac based signals.

Figure 5:
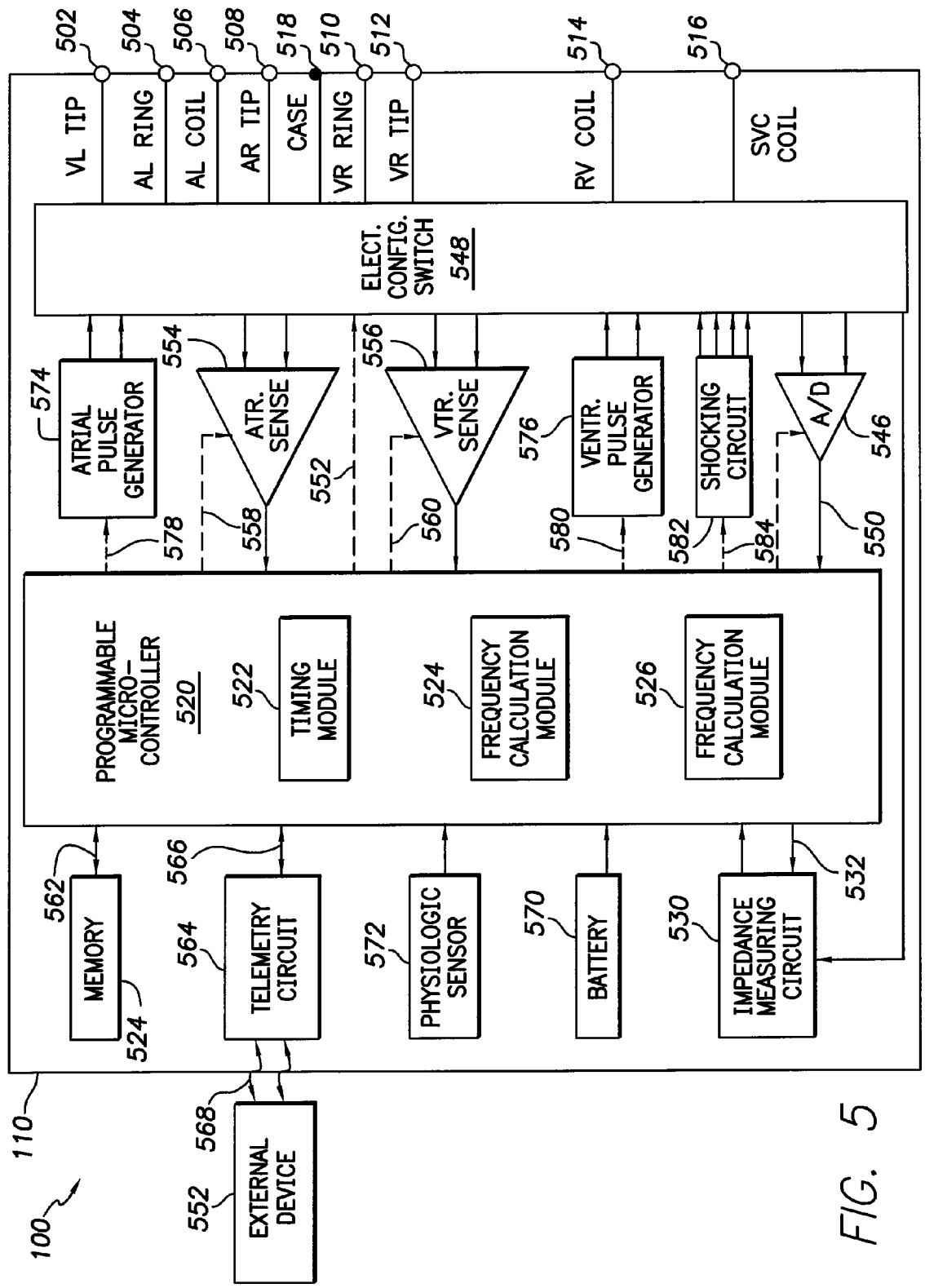
FIG. 5 illustrates a block diagram of exemplary internal components of the IMD shown in FIG. 1 in accordance with one embodiment.

FIG. 5 illustrates a block diagram of exemplary internal components of the IMD 100. The IMD 100 includes the housing 110 that includes a left ventricle tip input terminal ($V_L$ TIP) 502, a left atrial ring input terminal ($A_L$ RING) 504, a left atrial coil input terminal ($A_L$ COIL) 506, a right atrial tip input terminal ($A_R$ TIP) 508, a right ventricular ring input terminal ($V_R$ RING) 510, a right ventricular tip input terminal ($V_R$ TIP) 512, an RV coil input terminal 514 and an SVC coil input terminal 516. A case input terminal 518 may be coupled with the housing 110 of the IMD 100. The input terminals 502-518 may be electrically coupled with the electrodes 112-128 (shown in FIG. 1).

The IMD 100 includes a programmable microcontroller 520, which controls the operation of the IMD 100. The microcontroller 520 (also referred to herein as a processor, processor module, or unit) typically includes a microprocessor, or equivalent control circuitry, and may be specifically designed for controlling the delivery of stimulation therapy and may further include RAM or ROM memory, logic and timing circuitry, state machine circuitry, and I/O circuitry. The microcontroller 520 may include one or more modules and processors configured to perform one or more of the operations described above in connection with the method 200.

A timing module 522 measures the time intervals 342, 344, 346, 348, 350, 352 (shown in FIG. 3) of the signals 300 (shown in FIG. 3). For example, the timing module 522 may determine the time period between consecutive crossings of a threshold by a signal waveform segment. As described above, the timing module 522 may measure the time between a waveform segment 314, 316, 318, 320, 322, 324, 326, 328, 330, 332, 336, 338 (shown in FIG. 3) extending above and then falling below the upper threshold 400 (shown in FIG. 4) or falling below and then rising above the lower threshold 402 (shown in FIG. 4).

A frequency calculation module 524 determines the dominant frequencies 362, 364, 366, 368, 370, 372 (shown in FIG. 3) of the time intervals 342, 344, 346, 348, 350, 352 (shown in FIG. 3) identified by the timing module 522. As described above, the frequency calculation module 524 may calculate the dominant frequencies 362, 364, 366, 368, 370, 372 based on the time period over which the time intervals 342, 344, 346, 348, 350, 352 extend.

An event identification module 526 identifies cardiac events based on the dominant frequencies 362, 364, 366, 368, 370, 372 (shown in FIG. 3). As described above, the event identification module 526 may compare the dominant frequencies 362, 364, 366, 368, 370, 372 to one or more predetermined patterns to determine if the dominant frequencies 362, 364, 366, 368, 370, 372 match one or more of the patterns. If the dominant frequencies 362, 364, 366, 368, 370, 372 match a pattern, the event identification module 526 may classify the dominant frequencies 362, 364, 366, 368, 370, 372 as corresponding to a cardiac event, such as a waveform segment. Alternatively, the event identification module 526 may identify cardiac events based on the time intervals 342, 344, 346, 348, 350, 352 (shown in FIG. 3) instead of the dominant frequencies 362, 364, 366, 368, 370, 372, as described above.

The microprocessor 520 receives signals from the electrodes 112-128 (shown in FIG. 1) via an analog-to-digital (A/D) data acquisition system 546. The signals 300 (shown in FIG. 3) are sensed by the electrodes 112-128 and communicated to the data acquisition system 546. The signals 300 are communicated through the input terminals 502-516 to an electronically configured switch bank, or switch, 548 before being received by the data acquisition system 546. The data acquisition system 546 converts the raw analog data of the signals obtained by the electrodes 112-128 into digital signals 550 and communicates the signals 550 to the microcontroller 520. A control signal 548 from the microcontroller 520 determines when the data acquisition system 546 acquires signals 300, stores the signals 550 in a memory 524, or transmits data to an external device 552.

The switch 548 includes a plurality of switches for connecting the desired electrodes 112-128 (shown in FIG. 1) and input terminals 502-518 to the appropriate I/O circuits. The switch 548 closes and opens switches to provide electrically conductive paths between the circuitry of the IMD 100 and the input terminals 502-518 in response to a control signal 552. An atrial sensing circuit 554 and a ventricular sensing circuit 556 may be selectively coupled to the leads 104-108 (shown in FIG. 1) of the IMD 100 through the switch 548 for detecting the presence of cardiac activity in the chambers of the heart 102 (shown in FIG. 1). The sensing circuits 554, 556 may sense the signals that are analyzed by the microcontroller 520. Control signals 558, 560 from the microcontroller 520 direct output of the sensing circuits 554, 556 that are connected to the microcontroller 520.

An impedance measuring circuit 530 may be enabled by the microcontroller 520 via a control signal 532. The impedance measuring circuit 530 may be electrically coupled to the switch 548 so that an impedance vector between any desired pairs of electrodes 112-128 (shown in FIG. 1) may be obtained. The IMD 100 additionally includes a battery 570 that provides operating power to the circuits shown within the housing 500, including the microcontroller 520. The IMD 100 includes a physiologic sensor 572 that may be used to adjust pacing stimulation rate according to the exercise state of the patient.

The memory 524 may be embodied in a computer-readable storage medium such as a ROM, RAM, flash memory, or other type of memory. The microcontroller 520 is coupled to the memory 524 by a suitable data/address bus 562. The memory 524 may store programmable operating parameters and thresholds used by the microcontroller 520, as required, in order to customize the operation of IMD 100 to suit the needs of a particular patient. For example, the memory 524 may store data such as the predetermined patterns that are compared to the dominant frequencies 362, 364, 366, 368, 370, 372 (shown in FIG. 3) and/or time intervals 342, 344, 346, 348, 350, 352 (shown in FIG. 3), the upper and lower thresholds 400, 402 (shown in FIG. 4) of the zero zone 404 (shown in FIG. 4), and the like. The operating parameters of the IMD 100 and thresholds may be non-invasively programmed into the memory 524 through a telemetry circuit 564 in communication with the external device 552, such as a trans-telephonic transceiver or a diagnostic system analyzer. The telemetry circuit 564 is activated by the microcontroller 520 by a control signal 566. The telemetry circuit 564 allows data and status information relating to the operation of IMD 100 to be sent to the external device 552 through an established communication link 568.

An atrial pulse generator 574 and a ventricular pulse generator 576 generate pacing stimulation pulses for delivery by the IMD 100 via the switch bank 548. The pulse generators 574, 576 are controlled by the microcontroller 520 via appropriate control signals 578, 580 respectively, to trigger or inhibit the stimulation pulses. To provide the function of an implantable cardioverter/defibrillator (ICD), the microcontroller 520 may control a shocking circuit 582 by way of a control signal 584. The shocking pulses are applied to the patient's heart 102 (shown in FIG. 1) through at least two shocking electrodes, such as the left atrial coil electrode 120 (shown in FIG. 1), the RV coil electrode 126 (shown in FIG. 1), and/or the SVC coil electrode 128 (shown in FIG. 1).

Figure 6:
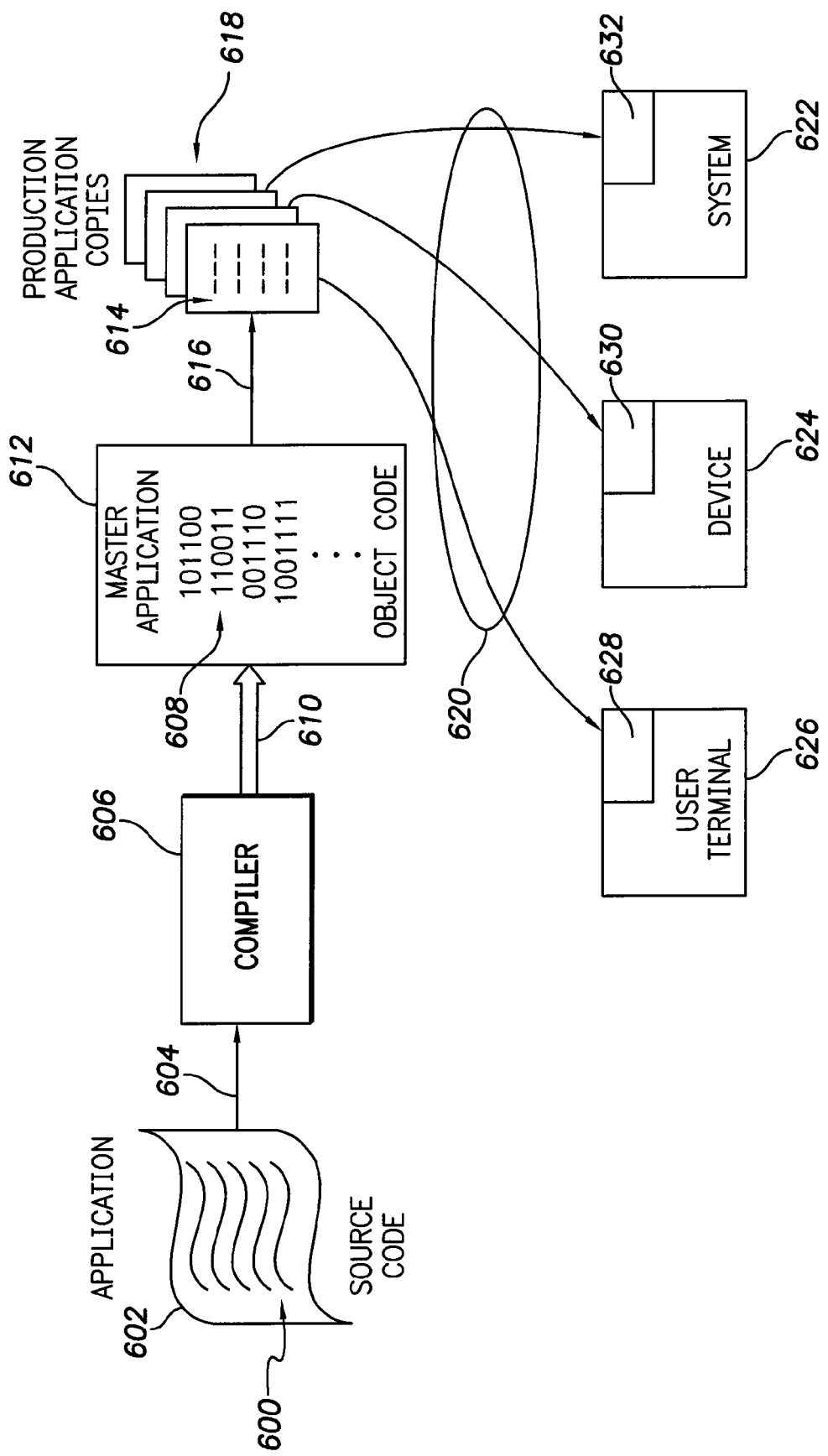
FIG. 6 illustrates a block diagram of example manners in which embodiments of the present invention may be stored, distributed, and installed on a computer-readable medium.

FIG. 6 illustrates a block diagram of example manners in which embodiments of the present invention may be stored, distributed, and installed on a computer-readable medium. In FIG. 6, the "application" represents one or more of the methods and process operations discussed above. The application is initially generated and stored as source code 600 on a source computer-readable medium 602. The source code 600 is then conveyed over path 604 and processed by a compiler 606 to produce object code 608. The object code 608 is conveyed over path 610 and saved as one or more application masters on a master computer-readable medium 612. The object code 608 is then copied numerous times, as denoted by path 614, to produce production application copies 616 that are saved on separate production computer-readable media 618. The production computer-readable media 618 are then conveyed, as denoted by path 620, to various systems, devices, terminals and the like.

A user terminal 622, a device 624 and a system 626 are shown as examples of hardware components, on which the production computer-readable medium 618 are installed as applications (as denoted by 628 through 632). For example, the production computer-readable medium 618 may be installed on the IMD 100 (shown in FIG. 1) and/or the microcontroller 520 (shown in FIG. 5). Examples of the source, master, and production computer-readable medium 602, 612, and 618 include, but are not limited to, CDROM, RAM, ROM, Flash memory, RAID drives, memory on a computer system, and the like. Examples of the paths 604, 610, 614, and 620 include, but are not limited to, network paths, the internet, Bluetooth, GSM, infrared wireless LANs, HIPERLAN, 3G, satellite, and the like. The paths 604, 610, 614, and 620 may also represent public or private carrier services that transport one or more physical copies of the source, master, or production computer-readable media 602, 612 or 618 between two geographic locations. The paths 604, 610, 614, and 620 may represent threads carried out by one or more processors in parallel. For example, one computer may hold the source code 600, compiler 606, and object code 608. Multiple computers may operate in parallel to produce the production application copies 616. The paths 604, 610, 614, and 620 may be intra-state, inter-state, intra-country, inter-country, intra-continental, inter-continental, and the like.

The operations noted in FIG. 6 may be performed in a widely distributed manner world-wide with only a portion thereof being performed in the United States. For example, the application source code 600 may be written in the United States and saved on a source computer-readable medium 602 in the United States, but transported to another country (corresponding to path 604) before compiling, copying and installation. Alternatively, the application source code 600 may be written in or outside of the United States, compiled at a compiler 606 located in the United States and saved on a master computer-readable medium 612 in the United States, but the object code 608 transported to another country (corresponding to path 614) before copying and installation. Alternatively, the application source code 600 and object code 608 may be produced in or outside of the United States, but production application copies 616 produced in or conveyed to the United States (for example, as part of a staging operation) before the production application copies 616 are installed on user terminals 622, devices 624, and/or systems 626 located in or outside the United States as applications 628 through 632.

As used throughout the specification and claims, the phrases "computer-readable medium" and "instructions configured to" shall refer to any one or all of (i) the source computer-readable medium 602 and source code 600, (ii) the master computer-readable medium and object code 608, (iii) the production computer-readable medium 618 and production application copies 616, and/or (iv) the applications 628 through 632 saved in memory in the terminal 622, device 624, and system 626.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An implantable medical device comprising:
   one or more leads comprising electrodes configured to be positioned within a heart, the electrodes capable of sensing signals derived from the heart, the signals comprising waveform segments that comprise a portion of a cardiac cycle;
   a timing module to determine when each of the waveform segments crosses a plurality of thresholds and to measure a time interval between at least two threshold crossings for each of the waveform segments, wherein the plurality of thresholds have different amplitude levels; and
   an event identification module to compare the time intervals to a predetermined pattern associated with a cardiac event, the event identification module to identify the cardiac event based on the time intervals and the predetermined pattern, wherein the cardiac event is selected from the group consisting of a QRS complex and a T-wave.

2. The implantable medical device of claim 1, further comprising a frequency calculation module to determine dominant frequencies of the signals based on the time intervals, wherein the event identification module compares the dominant frequencies to the pattern to determine if the dominant frequencies match the pattern.

3. The implantable medical device of claim 2, wherein the pattern represents at least one of a number of the dominant frequencies identified by the frequency calculation module within a predetermined time window or a magnitude of one or more of the dominant frequencies.

4. The implantable medical device of claim 1, wherein the timing module measures the time intervals as periods between the signals rising above the threshold followed by the signals dropping below the threshold.

5. The implantable medical device of claim 1, wherein the timing module measures the time intervals as periods between the signals falling below the threshold followed by the signals rising above the threshold.

6. The implantable medical device of claim 1, wherein the timing module measures the time intervals as periods that the signals extend above a zero zone of signals, the zero zone extending between an upper threshold and a lower threshold.

7. The implantable medical device of claim 1, wherein the event identification module identifies the waveform segments of the signals based on the time intervals.

8. The implantable medical device of claim 1, wherein the pattern represents a number of the time intervals occurring during a predetermined time window.

9. The implantable medical device of claim 1, wherein the timing module measures the time intervals between the threshold crossings by the waveform segments.

10. A method for identifying cardiac events, the method comprising:
    sensing signals derived from a heart that include waveform segments that comprise a portion of a cardiac cycle;
    determining when each of the waveform segments crosses a plurality of thresholds, wherein the plurality of thresholds have different amplitude levels;
    measuring a time interval between at least two threshold crossings for each of the waveform segments;
    comparing the time intervals to a predetermined pattern associated with a cardiac event; and
    identifying the cardiac event based on the time intervals and the predetermined pattern, wherein the cardiac event is selected from the group consisting of a QRS complex and a T-wave.

11. The method of claim 10, further comprising determining dominant frequencies of the signals based on the time intervals, wherein the identifying operation comprises comparing the dominant frequencies to the pattern to determine if the dominant frequencies match the pattern.

12. The method of claim 11, wherein the pattern represents at least one of a number of the dominant frequencies identified by the frequency calculation module within a predetermined time window or a magnitude of one or more of the dominant frequencies.

13. The method of claim 10, wherein the time intervals are periods between the signals rising above the threshold followed by the signals falling below the threshold.

14. The method of claim 10, wherein the time intervals are periods between the signals falling below the threshold followed by the signals rising above the threshold.

15. The method of claim 10, wherein the time intervals are periods that the signals extend above a zero zone of signals, the zero zone extending between an upper threshold and a lower threshold.

16. The method of claim 10, wherein the identifying operation identifies the waveform segments of the signals based on the time intervals.

17. The method of claim 10, wherein the pattern represents a number of the time intervals occurring during a predetermined time window.

* * * * *